United States Patent
Knuebel et al.

(10) Patent No.: US 12,121,133 B2
(45) Date of Patent: Oct. 22, 2024

(54) METHOD FOR DETERMINING A GREYNESS LEVEL OF A STRAND OF HAIR

(71) Applicant: Henkel AG & Co. KGaA, Duesseldorf (DE)

(72) Inventors: Hans Georg Knuebel, Duesseldorf (DE); Lucile Bonnin, Duesseldorf (DE); Astrid Kroos, Monheim (DE)

(73) Assignee: HENKEL AG & CO. KGAA, Duesseldorf, NY (US)

( * ) Notice: Subject to any disclaimer, the term of this patent is extended or adjusted under 35 U.S.C. 154(b) by 666 days.

(21) Appl. No.: 17/414,293

(22) PCT Filed: Dec. 17, 2019

(86) PCT No.: PCT/EP2019/085603
§ 371 (c)(1),
(2) Date: Jun. 15, 2021

(87) PCT Pub. No.: WO2020/127228
PCT Pub. Date: Jun. 25, 2020

(65) Prior Publication Data
US 2022/0061503 A1    Mar. 3, 2022

(30) Foreign Application Priority Data
Dec. 18, 2018   (EP) .................................... 18213515

(51) Int. Cl.
*G06K 9/38*    (2006.01)
*A45D 44/00*   (2006.01)
(Continued)

(52) U.S. Cl.
CPC .......... *A45D 44/005* (2013.01); *A61B 5/1034* (2013.01); *A61B 5/448* (2013.01);
(Continued)

(58) Field of Classification Search
CPC ........ G06V 10/20; G06V 10/22; G06V 10/25; G06V 10/28; G06V 10/50; G06V 10/507;
(Continued)

(56) References Cited

U.S. PATENT DOCUMENTS

| | | | | |
|---|---|---|---|---|
| 4,807,163 A | * | 2/1989 | Gibbons | G06V 10/40 382/173 |
| 6,067,504 A | * | 5/2000 | MacFarlane | G01N 21/84 356/402 |

(Continued)

FOREIGN PATENT DOCUMENTS

WO     03012728 A1    2/2003

OTHER PUBLICATIONS

Arno Zinke, Tomás Lay, Anton Andriyenko, "A Practical Approach for Photometric Acquisition of Hair Color", ACM Transactions on Graphics, vol. 28, No. 5, Article 165, Dec. 2009, pp. 165:1-165:10 (Year: 2009).*

(Continued)

*Primary Examiner* — Eric Rush
(74) *Attorney, Agent, or Firm* — Lorenz & Kopf, LLP (57) ABSTRACT

A method for determining a greyness level of a strand of hair and a system adapted to implement this method are provided. First, an image of the strand of hair representing it according to a predefined representation standard is obtained. The image comprises a portion representing the strand of hair with pixels. Then, for each pixel of the portion, a luminance value is determined. After that an amount of pixels in the portion for which the determined luminance value is above a threshold luminance value is determined. Finally, the greyness level of the strand of hair is determined by estimating a ratio of the determined amount of pixels over a total amount of pixels in the portion.

19 Claims, 5 Drawing Sheets

(51) Int. Cl.
| | |
|---|---|
| *A61B 5/00* | (2006.01) |
| *A61B 5/103* | (2006.01) |
| *G01J 3/46* | (2006.01) |
| *G01J 3/52* | (2006.01) |
| *G06T 5/40* | (2006.01) |
| *G06T 5/92* | (2024.01) |
| *G06T 7/00* | (2017.01) |
| *G06T 7/11* | (2017.01) |
| *G06T 7/90* | (2017.01) |
| *G06V 10/28* | (2022.01) |
| *G06V 10/50* | (2022.01) |
| *G06V 10/56* | (2022.01) |

(52) U.S. Cl.
CPC . *G01J 3/46* (2013.01); *G01J 3/52* (2013.01); *G06T 5/40* (2013.01); *G06T 5/92* (2024.01); *G06T 7/0002* (2013.01); *G06T 7/11* (2017.01); *G06T 7/90* (2017.01); *G06V 10/28* (2022.01); *G06V 10/50* (2022.01); *G06V 10/56* (2022.01); *A45D 2044/007* (2013.01); *G06T 2207/10024* (2013.01); *G06T 2207/30196* (2013.01)

(58) Field of Classification Search
CPC ........ G06V 10/56; G06V 10/60; G06V 40/16; G06V 40/161; G06V 40/162; G06V 40/171; G06T 5/40; G06T 5/90; G06T 5/92; G06T 5/94; G06T 7/0002; G06T 7/10; G06T 7/11; G06T 7/136; G06T 7/70; G06T 7/90; G06T 2207/10004; G06T 2207/10024; G06T 2207/30088; G06T 2207/30196; A45D 44/005; A45D 2044/007; A61B 5/103; A61B 5/1032; A61B 5/1034; A61B 5/44; A61B 5/448; G01J 3/46; G01J 3/463; G01J 3/52; G01J 3/524; G01J 2003/466; G01N 21/25; G01N 21/251; G01N 21/27; G01N 21/274; G01N 21/278; G01N 21/29; G01N 21/293; G01N 21/84

USPC ....... 382/100, 108, 162, 164–173, 190, 195, 382/224, 227, 228, 237, 251, 254, 382/260–262, 270–274, 276, 282, 312, 382/313, 325; 356/43–47, 243.5, 243.8, 356/402, 404–408, 421, 425; 345/426, 345/589–591, 593, 596, 597, 600, 603, 345/604; 209/576, 577, 580, 581

See application file for complete search history.

(56) References Cited

U.S. PATENT DOCUMENTS

| | | | | |
|---|---|---|---|---|
| 7,151,851 | B2* | 12/2006 | Ladjevardi | G06T 7/90 382/162 |
| 10,217,244 | B2* | 2/2019 | Kowalczyk | G06V 10/758 |
| 2006/0089555 | A1* | 4/2006 | Gummer | A61B 5/0059 600/476 |
| 2008/0260243 | A1* | 10/2008 | Occelli | G01J 3/462 382/165 |
| 2011/0218941 | A1* | 9/2011 | Asaoka | A61B 5/448 382/128 |
| 2012/0320191 | A1* | 12/2012 | Meschkat | G01N 21/84 348/135 |
| 2014/0119642 | A1* | 5/2014 | Lee | G06V 40/171 382/159 |
| 2018/0116583 | A1* | 5/2018 | Cook | G06T 7/62 |

OTHER PUBLICATIONS

EPO, International Search Report issued in International Application No. PCT/EP2019/085603, dated Mar. 12, 2020.

Zinke et al.: "A practical approach for photometric acquisition of hair color", ACM SIGGRAPH Asia 2009 Papers On, SIGGRAPH Asia, Jan. 2009, p. 1, XP055098824.

Lin Li, et al., Applied Optics (5th Edition), The Twelfth Five-Year Plan, State level Planning Textbook for Undergraduate Programs in General Higher Education, Beijing Higher Education High-Quality Teaching Materials, Beijing Institute of Technology Press, Chapter XIV, New Modern Optoelectronic Devices and Their Imaging Systems,. pp. 301-302, 2017.

* cited by examiner

METHOD FOR DETERMINING A GREYNESS LEVEL OF A STRAND OF HAIR

CROSS-REFERENCE TO RELATED APPLICATION

This application is a U.S. National-Stage entry under 35 U.S.C. § 371 based on International Application No. PCT/EP2019/085603, filed Dec. 17, 2019, which was published under PCT Article 21(2) and which claims priority to European Application No. 18213515.2, filed Dec. 18, 2018, which are all hereby incorporated in their entirety by reference.

TECHNICAL FIELD

The present disclosure relates to the field of characterization of hair color, in particular the determination of the ratio of white hairs in a hair strand. This ratio is generally referred to as a greyness level.

TECHNOLOGICAL BACKGROUND

Knowledge of one's hair state, and in particular hair color is important information to have for selecting the right hair treatment compositions among available products. A hair treatment product such as shampoo or hair coloration compositions (also called hair dyes) will have a different effect when applied to different users. Among the parameters that can have an impact on the selection of a hair treatment product, in particular a hair coloration product, the presence and amount of white hairs should be taken into account.

Traditionally, assessment of the greyness level of the hair of a user is done subjectively either by the user himself, or by a hair stylist, who has more experience in handling different hair types. However, such an approach requires the presence of an experienced professional and further remains a subjective assessment of a person's true hair greyness level.

A more objective approach might include using image analysis tools such as colorimetry to determine greyness levels. In particular an image of a hair strand can be analyzed to determine an average hair color value by calculating averages of the numerical components of the color of pixels in the image in a color space (for example the L*a*b color space where L stands for lightness, a stands for the green and red components and b for the blue and yellow components, or else RGB where R stands for red, G stands for green and B stands for blue).

Another pitfall of colorimetric measurements in determining greyness levels lies in the fact that measurement spots generally cover an area of 0.5 cm² to 1 cm². White hairs appear in a strand of hair as a random mixture of pigmented and non-pigmented fibers, giving rise to a "salt and pepper" impression. The colorimetric approach therefore averages the color without being able to individually count and distinguish white hair fibers from pigmented hair fibers.

In other words, colorimetry is unsuccessful in determining the greyness level of a user's hair.

Even if a high resolution camera is used, which can record pixels with a micrometer or sub-micrometer spatial resolution, an objective determination of the greyness level would lack precision because of the strong influence of illumination conditions and angle of view on the observed color, because differences in illumination conditions alter the measurements from one strand of hair to another.

A method is therefore sought in order to improve the objectivity and accuracy of the determination of greyness levels of strands of hair.

BRIEF SUMMARY

Systems, methods, and computer-readable storage mediums for determining grayness levels of hair are provided. In an exemplary embodiment, a method includes obtaining an image of a strand of hair, where the image represents the strand of hair according to a predetermined representation standard. The image includes a portion that represents the strand of hair with pixels. A luminance value is determined for each pixel of the portion, and an amount of the pixels in the portion with a luminance value above a threshold luminance value is also determined. The grayness level of the hair is determined by estimating a ratio of the amount of pixels having a luminance value above the threshold luminance value over a total amount of pixels in the portion.

A system for determining grayness levels of hair is provided in another embodiment. The system includes an image acquisition device that is configured to receive an image of a strand of hair according to a predefined representation standard, and a non-transitory data processing device capable of receiving data from the image acquisition device. The non-transitory data processing device is configured to select a portion within the image, where the portion represents the strand of hair with pixels, and determine a luminance value for each pixel of the portion. The data processing device is also configured to estimate an amount of pixels in the portion which have a luminance value above a threshold luminance value, and determine the grayness level of the hair by calculating a ratio of the amount of pixels in the portion with a luminance value above the threshold luminance value over a total amount of pixels in the portion.

A non-transitory computer readable storage medium for determining grayness of hair is provided in another embodiment. The computer readable storage medium includes instructions for how to determine the greyness level of hair. The instructions are for a method that includes obtaining an image of a strand of hair, where the image represents the strand of hair according to a predetermined representation standard. The image includes a portion that represents the strand of hair with pixels. The instructions further provide guidance for determining a luminance value for each pixel of the portion, and an amount of the pixels in the portion with a luminance value above a threshold luminance value is also determined. The grayness level of the hair is determined by estimating a ratio of the amount of pixels having a luminance value above the threshold luminance value over a total amount of pixels in the portion.

BRIEF DESCRIPTION OF THE DRAWINGS

The present disclosure will hereinafter be described in conjunction with the following drawing figures, wherein like numerals denote like elements, and:

FIG. 1b is a histogram of the luminance of pixels from the image of FIG. 1a;

For the sake of clarity, dimensions of features represented on these figures may not necessarily correspond to the real-size proportion of the corresponding elements.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

In order to overcome the above drawbacks, the present disclosure provides a method for determining a greyness level of a strand of hair, the method comprising:
  obtaining an image of the strand of hair, the image representing the strand of hair according to a predefined representation standard, the image comprising a portion representing the strand of hair with pixels;
  determining, for each pixel of the portion, a luminance value;
  determining an amount of pixels in the portion for which the determined luminance value is above a threshold luminance value;
  determining the greyness level of the strand of hair by estimating a ratio of the determined amount of pixels over a total amount of pixels in the portion.

This method adds objectivity to the determination of the greyness level of the hair of a user, based on an analysis of the luminosity observed on images of one of the user's strands of hair. It is assumed that white hair fibers appear brighter, that is to say with a higher luminosity, than pigmented hair fibers. It is therefore possible to distinguish image pixels corresponding to white hair fibers from pixels corresponding to pigmented hair fibers based on the luminance thereof. However, this should be performed on images that represent fibers according to a predefined representation standard. The term "predefined representation standard" is to be understood, in the context of the present disclosure, as reverting to the geometrical and physical conditions under which the hair fibers were imaged. For example, such conditions can encompass: the resolution of the image (magnification), illumination conditions (spectrum of the light incident on the strand of hair, light intensity), and the perspective from which the strand of hair is represented (angle of view, distance between an image acquisition tool and the fibers of the strand of hair). When such conditions are predefined, it is possible to establish a reliable workflow to determine the greyness level of any strand of hair. For that, a reference value for a threshold luminance, capable of distinguishing pigmented hair fibers from white hair fibers on any image, is used. One approach includes fixing this threshold luminosity value to a luminosity value which can discriminate between pigmented hair fibers and white hair fibers on an image of a strand of hair whose greyness level is already known. This can for example be done by using image analysis tools to determine the distribution of all luminance values and see which ones belong to the brightest pixels of the image and which ones belong to the darkest ones. The threshold value is located at the luminosity level above which the percentage of pixels having a higher luminosity is equal to the percentage of white hair fibers in a strand of hair whose greyness level is known. Other definitions for the threshold luminance value can be used, for example if the image representing the strand of hair is so highly contrasted that there is a clear distinction between pixels belonging to pigmented fibers and pixels belonging to white hair fibers. In that case, the threshold luminance value can be set at an intermediary luminance value between that of the brightest pixel and the darkest pixel for example.

It is to be noted that the "portion of the image" can also be the entire image itself, and not just a sub-element thereof.

According to an embodiment, the threshold luminance value is set as a median luminance value measured on an image of a reference strand of hair having a known proportion of white hair fibers equal to 50% of a total amount of hair fibers in the reference strand of hair.

Such a definition of the threshold luminance value can be easily fixed by mixing any type of hair fibers with an equal number of white hair fibers and measuring the median luminance value across all pixels of a portion of an image of the thus obtained reference strand of hair. The conditions in which the reference strand of hair was imaged fixes the predefined representation standard for further measurements conducted on hair strands of unknown greyness level. The threshold luminance value can serve as a reference for all further measurements provided they are conducted on images of hair strands representing hair fibers in the predefined representation standard, or provided that they are converted into a format corresponding to the predefined representation standard.

According to an embodiment, the method may further comprise:
  setting the threshold luminance value depending on a color of pigmented fibers of the strand of hair.

Different hair fibers reflect light in different ways and appear with different luminance values on pixels of an image. It is therefore advantageous to set the threshold luminance value in accordance with the color of the pigmented fibers of the hair strand. For example, the threshold luminance value may be increasing in consecutive order, depending on the color of the pigmented fibers of the hair strand, classified as follows: black, dark brown, light brown, dark blond, medium blond, light blond.

According to an embodiment, the method may further comprise:
  obtaining an image of a reference strand of hair of known greyness level, the image representing the reference strand of hair according to the predefined representation standard, the image comprising a reference portion representing the reference strand of hair with pixels;
  determining, for each pixel of the reference portion, a luminance value;
  arranging the determined luminance values according to percentiles;
  setting the threshold luminance value as being a luminance value observed for a percentile of luminance values equal to a total percentage of pigmented hair fibers in the reference strand of hair.

It is not necessary to use a reference strand of hair for which half of all hair fibers are white hair fibers. Reference strands of hair having any proportion of white hair fibers can be used to determine the threshold luminance value. However, when the proportion of white hair fibers is not equal to 50% of the total amount of hair fibers, the median luminosity value measured for pixels of the portion of the reference strand of hair is not a relevant value any more. Instead, more reliable results are obtained by ranking luminance values according to percentiles. For example, if a reference strand of hair comprises 70% of white hair fibers, its comprises 30% of pigmented hair fibers. The luminance value corresponding to the 30$^{th}$ percentile of luminance values provides a critical luminance value. At the critical luminance value of this example, 30% of all pixels have a luminance value below that critical threshold value, and can thus be identified as corresponding to pigmented hair fibers (representing on average 30% of all the "darker" information on the portion of the image) and 70% of all pixels have a luminosity higher than the critical luminance value and correspond to the "brighter" information on the portion of the image, associated with white hair fibers. The critical luminance value is then set as the threshold luminance value.

According to an embodiment, the method may further comprise:
    obtaining at least two reference strands of hair of different and known greyness;
    obtaining, for each reference strand of hair, an image representing the strand of hair according to the predefined representation standard, the image comprising a reference portion representing the reference strand of hair with pixels;
    determining, for each pixel of the reference portion of each image, a luminance value;
    arranging, for the reference portion of each image, the determined luminance values according to percentiles;
    determining, for the reference portion of each image, a critical luminance value as being a luminance value observed for a percentile of luminance values equal to a total percentage of pigmented hair fibers in the reference strand of hair, and
    setting the threshold luminance value as being an average value of determined critical luminance values.

By increasing the number of reference strands of hair used to determine a critical threshold value, a higher degree of precision can be reached for determining the threshold luminance value. Theoretically, all critical luminance values should be the same, or substantially identical. An average value might reduce any noise in the determination of the threshold luminance value.

According to an embodiment, the threshold luminance value may be set using at least five reference strands of different and known greyness levels.

Using five reference strands allows a more precise determination of the threshold luminance value by averaging the critical luminance values determined for each reference strand of hair. In particular, it is possible to use strands of hair whose greyness levels cover a broad range of white hair proportions, for example 10%, 30%, 50%, 70% and 90%.

According to an embodiment, the method may further comprise:
    setting a threshold luminance value for each reference strand of hair of a set of reference strands of hair of known greyness value and comprising different hair colors.

According to an embodiment, the method may further comprise:
    converting a color of each pixel inside the portion of the image into a greyscale.

By converting the colored image into a greyscale image, further precision can be added to the determination of the greyness level of the hair strand. Indeed, shades of grey offer a more standardized approach for measuring the luminance of pixels representing hair fibers than colors. Blond hair fibers for example would typically appear as having a higher luminance on an image than black or brown hair fibers, thereby altering the accuracy of the determination of the greyness level. It is alternatively also possible to determine a threshold luminance value for each type of hair color to also improve accuracy of the method.

According to an embodiment, the method may further comprise:
    obtaining a raw image of the strand of hair, the raw image representing the strand of hair and a calibration bar of known dimensions and color;
    converting the raw image by adjusting representation parameters of the raw image using image processing capable of modifying at least one among angle of view, magnification and luminosity of the raw image in order to represent the strand of hair according to the predefined representation standard, the representation parameters including at least angle of view and magnification.

Using a calibration bar with a known color, shape, size and optionally of known light reflection properties, it is possible to circumvent the need to acquire images using fixed representation parameters. Instead, the calibration bar can provide the required information on the perspective, magnification and lighting condition that were used when acquiring the image so that the image can be processed and corrected from its raw state to a converted state compatible with the predefined representation standard.

The image processing capable of modifying at least one among angle of view, magnification and luminosity of the raw image can typically be software used to tilt or add a deformation of the image, for example shrinking an upper portion and magnifying a lower portion to simulate a change in the angle of view Luminosity of the raw image can be changed using a gamma parameter in a software to process images. Different masks can be applied to change properties of pixels within the image.

According to an embodiment, the predefined representation standard may comprise at least one of the following, or a combination thereof: angle of view, magnification, illumination conditions, spatial arrangement of fibers of the strand of hair, relative position of the strand of hair, and a light source illuminating the strand of hair, such as the spectrum and intensity of the light source.

Many different values can be selected for these parameters. Advantageously, these parameters should correspond to the values used when setting the threshold luminance value based on at least one reference strand of hair.

According to an embodiment, the method may further comprise:
    selecting the portion of the image representing the strand of hair with pixels, so that the portion comprises substantially parallel hair fibers.

It is particularly advantageous to avoid having overlapping hair fibers in the portion of the image. The strand of hair can for that matter for example rest on a substrate which helps arrange the hair fibers substantially parallel to each other. Although hair thickness does not affect the outcome of the estimation of the greyness level, it is preferable not to include sections of hair fibers that may have a different thickness to the lengths of the hair. For example hair roots or hair tips can be avoided in favor of hair lengths. Should the hair strand be on a user's head, care should be taken not to include portions that comprise skin, or else further processing of the portion to eliminate such areas would be recommended.

The present disclosure also pertains to a system adapted to implement the method described above. In particular, such a system for determining a greyness level of a strand of hair may comprise:
- an image acquisition device, configured to receive an image of the strand of hair, the image representing the strand of hair according to a predefined representation standard;
- at least one non-transitory data processing device capable of receiving data from the image acquisition device and configured to:
- select a portion within the image, the portion representing the strand of hair with pixels;
- determine, for each pixel of the portion, a luminance value;
- estimate an amount of pixels in the portion for which the determined luminance value is above a threshold luminance value;
- determine the greyness level of the strand of hair by calculating a ratio of the estimated amount of pixels (which have a determined luminance value above the threshold luminance value) over a total amount of pixels in the portion.

The term "image acquisition device" can refer to an electronic component capable of receiving a prerecorded image in numerical form. In that case, the "image acquisition device" is a hardware component such as a circuit comprising a processor. It can also be a camera, photodetector or any other device capable of recording an image by measuring light reflected by the strand of hair. The optical resolution of this photodetector is advantageously at a micrometer or sub-micrometer level, in order to be able to detect individual hair fibers on the portion of the image. The "at least one non-transitory data processing device" is typically a hardware component such as a circuit comprising a processor which analyzes the numerical information of the image provided by the image acquisition device. When part of a device includes such items as a computer or a network of computers, different components can contribute to the implementation of the method. For example, a first circuit or computer may process the image to select a suitable portion therein. A second circuit or computer can build a datasheet of luminance properties of pixels and count those whose luminance is below the threshold luminance value.

According to an embodiment, the system may further comprise:
- a position selection mechanism, adapted to receive the image acquisition device and set it at a predefined distance, predefined position and predefined angle with respect to the strand of hair.

Such a position selection mechanism may for example be a physical element such as a frame. Such a frame may comprise adjustable elements to choose different positions and orientations for the image acquisition device with respect to the strand of hair. The mechanism may alternatively for example be comprised of a set of sensors recording a first configuration setting for a reference strand of hair and image acquisition device and checking whether further strands of hair and the image acquisition device are arranged according to the first configuration setting.

According to an embodiment, the system may further comprise:
- a light source, the light source being arranged at a predefined distance, predefined position and predefined angle with respect to the strand of hair and configured to emit light having predefined properties, selected from at least one of the following: spectrum of emitted light, and intensity of emitted light.

The light source may be ambient light, or an artificial light source whose properties are also predefined, in particular the spectrum of the emitted light, the intensity of the emitted light, and the orientation of the light source. Fixing the spectrum, intensity and orientation of the light source further improves accuracy of the method in determining the true greyness level of the hair strand.

According to an embodiment, the system may further comprise:
- a substrate comprising a curved surface, the curved surface being configured to receive the strand of hair.

This substrate may in particular have a receptacle with a curved surface on which hair fibers are intended to be placed in order to reflect light from a light source towards the image acquisition device from different incident angles. The light source may be ambient light, or a light source whose properties are also predefined, in particular the spectrum of the emitted light, the intensity of the emitted light, and the orientation of the light source. This allows a more accurate estimation of the greyness level by averaging the possible influence of lighting conditions. Indeed, hair fibers reflect light differently when light arrives from different incident angles. A curved surface for the strand of hair, for example a cylindrical surface, creates a gradient of incident angles for light projected onto the strand of hair and reflected towards the image acquisition device.

The present disclosure also pertains to a non-transitory computer readable storage medium having stored thereon a computer program comprising instructions for execution of a method for determining a greyness level of a strand of hair as described above.

In other words, the present disclosure also pertains to a computer program product comprising instructions for execution of a method for determining a greyness level of a strand of hair as described above.

The present disclosure provides a method which renders more objective and accurate the determination of the greyness level of hair fibers. The method relies on an estimation (by counting) of the number of bright pixels in an image of a strand of hair, obtained under predefined conditions forming a "calibration standard", also referred to as "predefined representation standard". The estimation of bright pixels is also guided by fixing a threshold luminance value which enables classifying pixels into two categories, as belonging to a white hair fiber or to a pigmented hair fiber. This threshold luminance value can be set by using reference strands of hair the greyness level of which is already know, and for which, under the "calibration standard", it is possible to determine how pixels on images of hair fibers can be identified as belonging to a white hair fiber or a pigmented hair fiber. This threshold value is set to the critical luminance level which is set at a limit to the luminance of pixels so that all pixels that have a higher luminance are identified as corresponding to a white hair fiber. At the critical luminance value, the proportion of more luminous pixels in the image is equal to the proportion of white hair fibers in the reference strand of hair.

The term "luminance" or brightness, may refer to the lightness L as represented in the L*a*b color space, or for example to the physical parameter describing brightness, that is to say the luminous flux per unit of solid angle, luminous intensity, expressed in candela cd, or the luminous flux per unit solid angle per unit projected source area expressed in candela per square meters. The term is not to be construed to these only definitions. For example it can be the equivalent of the lightness L in any other color space than the L*a*b color space, or it can be any other unit used to quantify the intensity of the optical signal perceived by a photodetector. Luminosity, brightness and luminance are interchangeable in this description and the appended claims.

In order to understand the method of the present disclosure, FIGS. 1a, 1b, and 2a-2f illustrate what happens when the properties of a strand of hair are analyzed using statistical tools applied on pixels of an image of such a strand of hair.

Figure 1A:
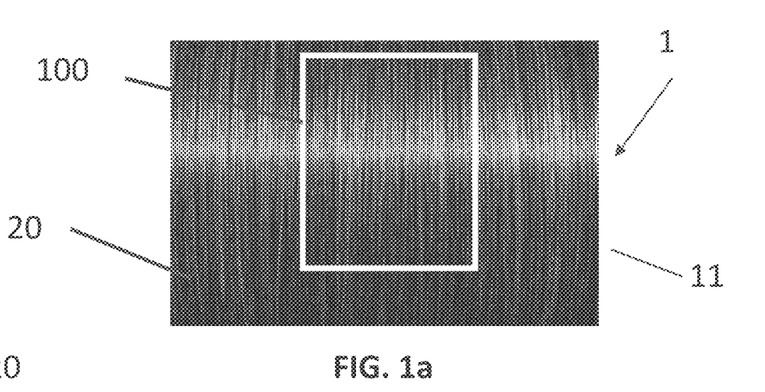
FIG. 1a is an illustration of an image of a strand of hair.

On FIG. 1a, an image 11 of a strand of hair 1 is represented. The strand of hair 1 was chosen deliberately to contain 50% of white hair fibers and 50% of pigmented hair fibers. The general impression when looking at image 11 is a "salt and pepper" look. The strand of hair rests on a substrate (not shown) having a curved surface, which gives rise to a gradient of brightness from the top to the bottom of the image 11. The perspective with which the image 11 was taken also gives rise to a bend on the hair fibers as seen in the edge 20 of image 11. When attempting to calculate the greyness level of this strand of hair, based on the image 11, it would be tempting to classify white pixels as belonging to white hair fibers and dark pixels as corresponding to pigmented hair fibers. The ratio of the white pixels over the total number of pixels would hint at the greyness level.

Figure 1B:
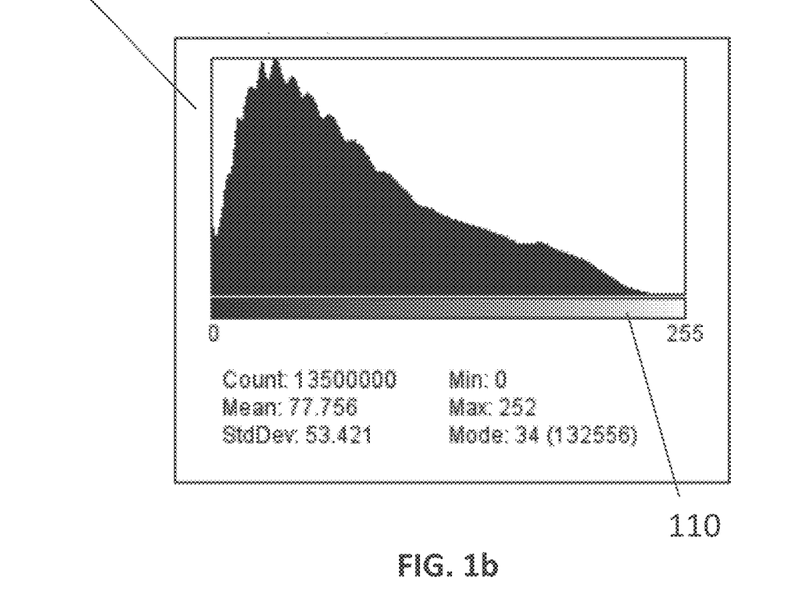

As seen on FIG. 1b, this approach would not be easy because there is no clear definition of what a white pixel is. FIG. 1b shows the histogram of luminance values (ranked from 0 to about 255, using the norm of the L*a*b color space for the L, lightness, component) for the pixels of image 11 represented on FIG. 1a. The horizontal axis 110 shows the luminance value from 0 to about 255 whereas the vertical axis 120 corresponds to the number of pixels having a determined luminance value. It can be seen that this histogram does not make a clear distinction between pixels belonging to white hair fibers and pixels belonging to pigmented hair fibers. A statistical analysis of the histogram shows that the mean luminosity is measured at 78. A closer look shows that this number is not the most suitable parameter to classify pixels into two categories identifying white hair fibers on one side and pigmented hair fibers on the other.

One source of uncertainty in this classification can come from edge effects as described above or influence from the illumination conditions. These effects can be mitigated by selecting a portion 100 of image 11 of FIG. 1a for example which comprises substantially parallel non-overlapping hair fibers.

Figure 2A:
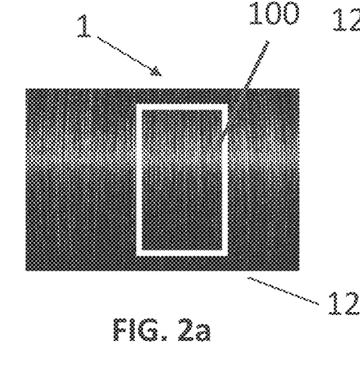
FIGS. 2a and 2c are illustrations of images of the strand of hair of FIG. 1a viewed under different illumination conditions.
Figure 2B:
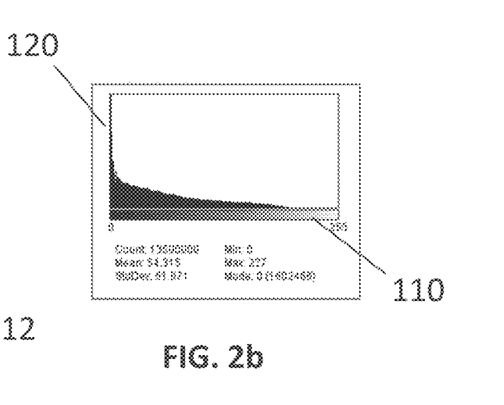
FIGS. 2b and 2d are histograms of the luminance of pixels from the images of FIGS. 2a and 2c respectively.
Figures 2C, 2D:
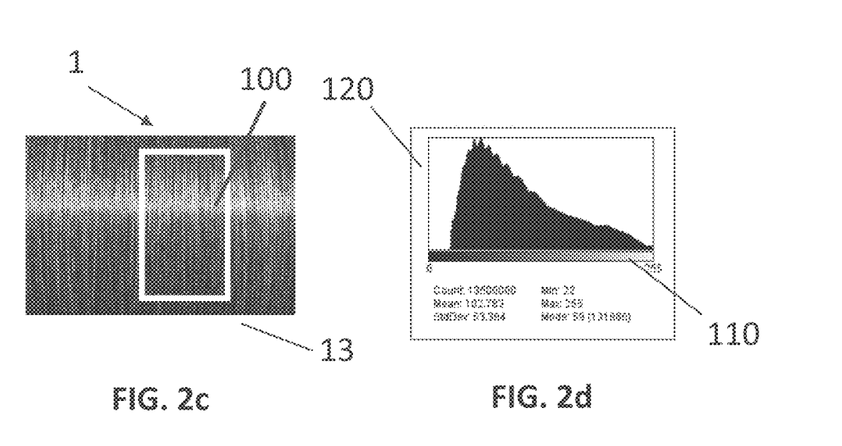

FIGS. 2a and 2c illustrate the same strand of hair 1 as in FIG. 1a under different illumination conditions. The perceived brightness on FIG. 2a showing an image 12 differs from that of FIG. 2c showing an image 13. Histograms of FIGS. 2b and 2d confirm these differences. In particular it can be seen that the mean luminance value is found to be at 54 for image 12 of FIG. 2a, the mean luminance value is found to be at 103 for image 13 of FIG. 2c. None of these values corresponds to the mean value 78 of FIG. 1b. Furthermore, the histograms show large disparities in the distribution of the luminance.

In order to add reliability to the determination of the greyness level, the present disclosure defines representation standards, which can also be referred to as calibration standard for images of hair strands. When all images are either acquired under predefined illumination conditions, at a predetermined distance from the strand of hair, with a predetermined magnification and under a predetermined viewing angle, then a histogram of luminance values for the strand of hair of FIG. 1a for example can serve as a reference to define a threshold luminance value. To do so, and knowing that in the example of the strand of hair 1 of FIG. 1, 50% of the brightness pixels are attributable to white hair and 50% of the darkest pixels are attributable to pigmented hair, the threshold luminance value can be fixed at the median value of luminance. An analysis of the statistics on luminance of pixels from image 11 leads to a median luminance value of 65, which differs substantially from the value, 78, provided by the mean luminance. It is to be noted that using a median luminance value in the example of FIG. 1 is a criterion which efficiently discriminates white hairs from pigmented hairs because the strand of hair 1 shown on FIG. 1 comprises a known proportion of white hairs and of pigmented hairs and that there are as many white hairs as there are pigmented hairs in this strand of hair 1.

Figure 3:
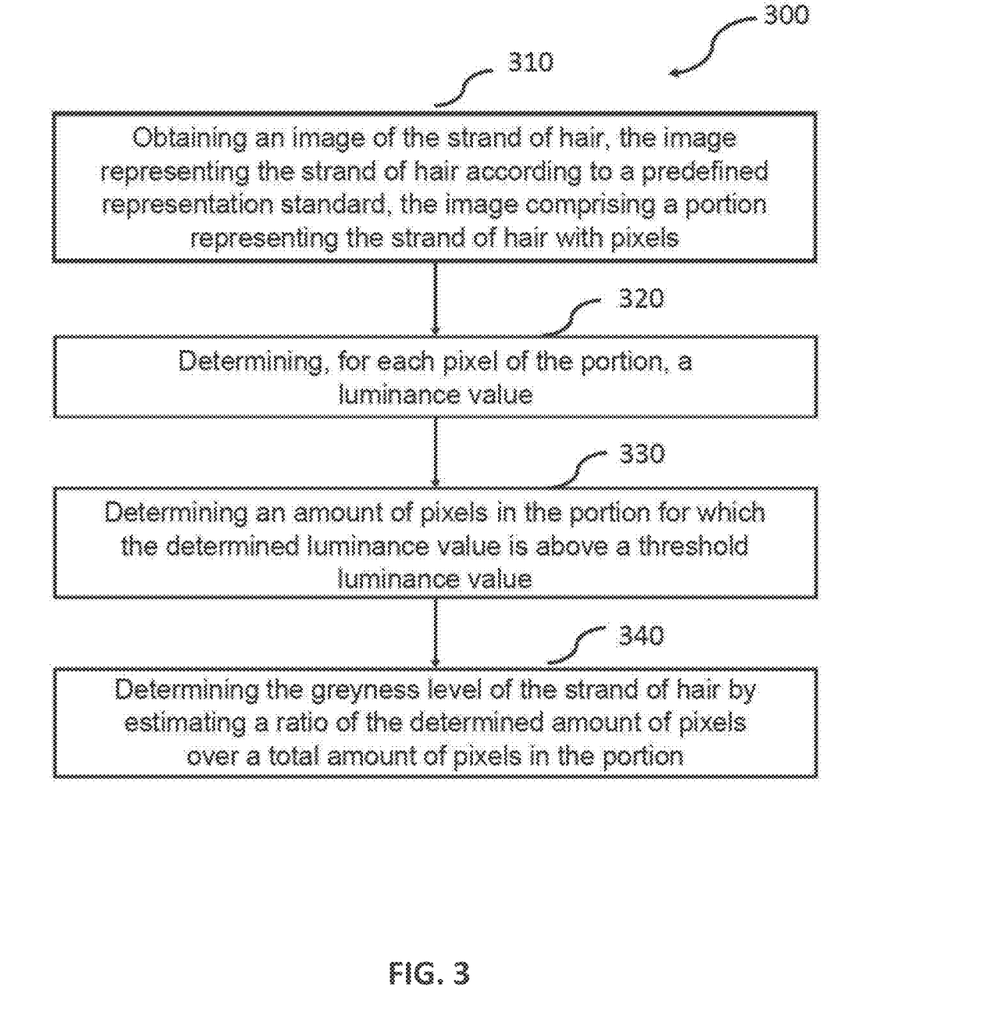
FIG. 3 is a schematic representation of a flowchart showing steps of a method according to an exemplary embodiment.

FIG. 3 summarizes in a flowchart the main steps that can be used to describe the method according to an embodiment of the present disclosure. First, the method 300 for determining the greyness level of a strand of hair may include obtaining 310 an image of the strand of hair, such that the image represents the strand of hair according to a predefined representation standard. This predefined representation standard can be used to define the conditions under which the image is taken, for example using a photodetector device. Alternatively, the predefined representation standard can serve as a reference for processing an existing image in order to convert it from a raw and unsuitable format and perspective into an image whose perspective, magnitude, resolution, and light conditions match those of the "predefined representation standard".

The predefined representation standard can encompass a number of parameters. For example, it can define an angle of view, magnification, illumination conditions, spatial arrangement of fibers of the strand of hair, relative position of the strand of hair and a light source illuminating the strand of hair, a spectrum and intensity of the light source.

When the image is not compatible with the predefined representation standard, or when there is no technique for reproducing closely enough the conditions under which the threshold luminance value was obtained, it is possible to take an image of the strand of hair further including a calibration object such as a calibration bar. Such an object has a known shape, dimensions, color, and light reflection properties and could further comprise inscriptions helping to change the perspective of the image in order to convert it into the predefined representation standard.

The image in the predetermined representation standard comprises in particular one portion 100, which can advantageously be selected to be void of skin, or roots, or tips. It is advantageously also void of the calibration bar if any was used to convert the image.

Once the image represents the strand of hair in the predefined representation standard, the method can be continued by determining 320, for each pixel of the portion 100, a luminance value.

This luminance value can be used at a further step, for determining 330 an amount of pixels in the portion for which the determined luminance value is above the threshold luminance value.

Finally, the method proceeds by determining 340 the greyness level of the strand of hair by estimating a ratio of the determined amount of pixels over the total amount of pixels in the portion 100, where the determined amount of pixels are the pixels determined to have a luminance value above the threshold luminance value.

Furthermore, the method may take into account the color of the pigmented fibers of the strand of hair. This color can be a relevant parameter in setting the threshold luminance value. Indeed, the luminance value of pixels of an image of blond hair fibers is similar to that of grey hair fibers, whereas the luminance value of black hair fibers is considerably smaller than that of grey hair fibers. It is therefore advantageous to determine a color of the pigmented hair fibers of a strand of hair, and to set the threshold luminance value accordingly. The following classification of hair fiber colors can be defined, from darkest to lightest: black, dark brown, medium brown, light brown, dark blond, medium blond, light blond. The threshold luminance value is set at increasingly higher values as the color of the pigmented hair fibers changes from black to light blond. It is to be noted that the method of the present disclosure overcomes this challenge by analyzing the distribution of luminance values within an image and setting the threshold luminance value at a value for which a ratio of pixels having a luminance higher than the threshold value is equal to the ratio of white hairs in a strand of hair of known greyness to which the method is applied.

In order to further improve accuracy of the determination of the greyness level, it is however also possible to analyze the color of the darkest pixels on an image of a strand of hair, in order to identify the corresponding color of the pigmented hair fibers. When the greyness of an unknown strand of hair is analyzed, the color of the darkest pixels is analyzed first to identify the corresponding color of the pigmented hairs. The luminance of pixels in the image of hair of unknown greyness is then analyzed using the method described above and with a threshold value fixed using strands of hair of known greyness values of similar hair colors. The term "similar" hair colors refers to hair colors whose distance in a color space to the hair color of the strand of hair of unknown greyness is minimized Accuracy of this method is then further improved, and it is then advantageous to determine threshold luminance values for a wide spectrum of pigmented hair colors.

Figure 4:
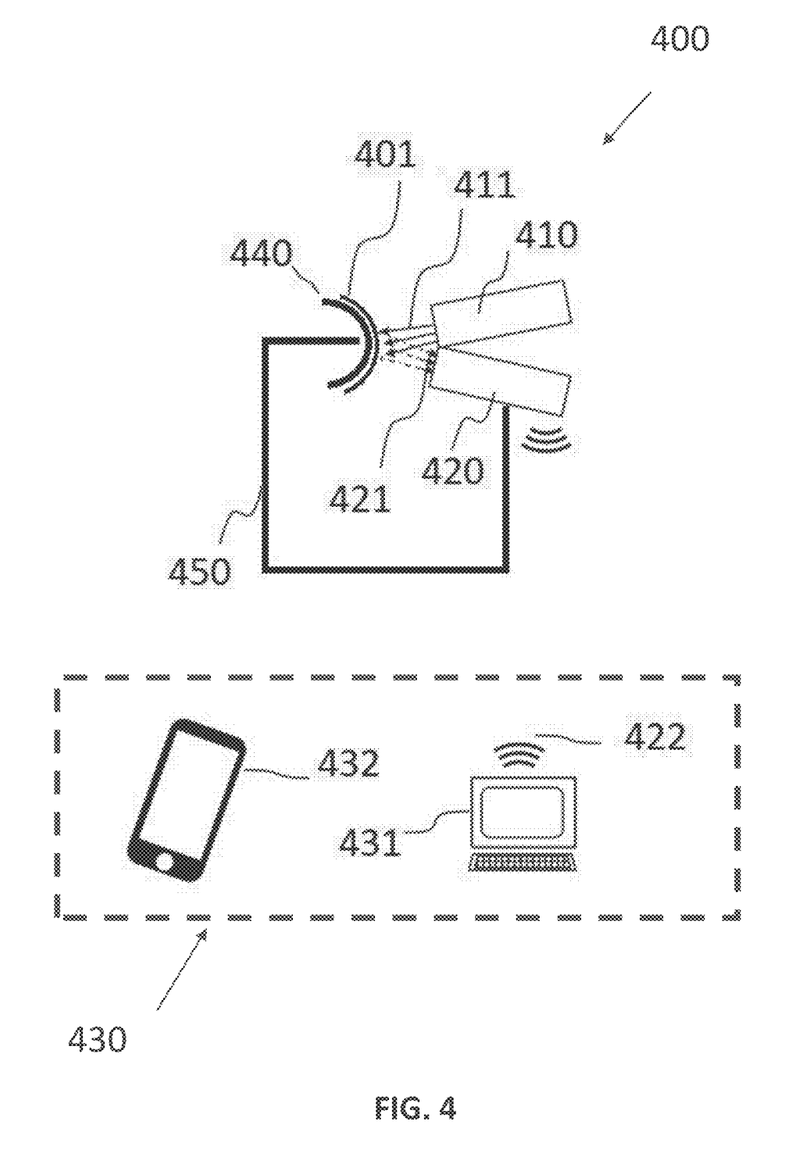
FIG. 4 is a schematic representation of a system according to an exemplary embodiment.

In order to implement this method 300, it is possible to use a system 400 such as that displayed on FIG. 4. FIG. 4 represents a hair fiber 401 shown from a side view, the hair fiber 401 being part of a strand of hair. The hair fiber 401, as well as the strand of hair of which it is a part, rests on a substrate 440 having a curved surface so that light incident on the strand of hair gets reflected into different directions, giving rise to fewer influences of the illumination conditions on the determination of the histogram of luminances of pixels. Incident light 411 can be either originating from ambient light, or from an artificial light source 410. Reflected light 421 can be detected by an image acquisition device 420, such as a photodetector, for example a camera or a charge coupled device. The image acquisition device can also be an electronic component that is merely capable of receiving a file via a wireless or via a wired connection, should the image already be accessible from a database for example.

The image that is obtained at the image acquisition device 420 is then transferred to a non-transitory data processing device 430, either wirelessly 422 or via a wired connection. The non-transitory data processing device 430 can for example be a computer 431, a processor a network of processors, electronic circuits or computers, which process the image so as to determine the greyness level of the strand of hair according to the steps described above.

Alternatively, the non-transitory data processing device 430 can also be a mobile device 432 such as a mobile phone, tablet or any similar device, or involve a mobile device 432 at any of the steps described above.

In order to ensure that the strand of hair, the image acquisition device 420 and optionally also the light source 410 are arranged in accordance with a predefine setup, enabling the generation of images compatible with the predefined representation standard, a position selection mechanism 450, such as a frame or an array of sensors can be used. If the position selection mechanism 450 is a frame, such as that schematically represented on FIG. 4, it may comprise adjustable elements in order to be able to select a distance and angle of view. Alternatively, the position selection mechanism can also be comprised of a set of sensors recording a first calibration setting for a reference strand of hair and image acquisition device and checking whether further strands of hair and the image acquisition device are arranged according to the first calibration setting.

A generalization of the method for setting a threshold luminance value is described below in connection with FIGS. 5a to 5d.

It is sufficient to estimate a luminance value observed on an image of a reference strand of hair of known greyness level to set the threshold luminance value. Once a histogram of pixel luminances is available, one should count the number of pixels for which the luminance is the brightness, up to a proportion of pixels equal to the proportion of white hair fibers known to be in the reference strand of hair.

FIGS. 5a to 5d shown images 14-17 of reference strands of hair having known greyness levels, converted from a color view into greyscale images. This conversion improves reliability and further standardizes the luminance values that are then observed on the image, regardless of the color of the pigmented hair fibers.

Figure 5A:
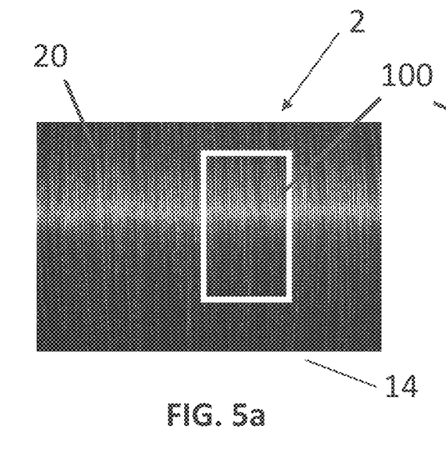
FIGS. 5a-5d are illustrations of greyscale images of reference strands of hair of known greyness level, comprising respectively 30%, 50%, 70% and 90% white hair fibers.

FIG. 5a shows a reference strand of hair 2 known to have a greyness level of 30%. In other words, 70% of the hair fibers are pigmented and 30% of the hair fibers in this reference strand of hair 2 are white hair fibers. Once an image 14 of this strand of hair is obtained in the predefined representation standard, a portion 100 can be selected. Alternatively, the portion 100 can encompass the whole image 14. Statistics are run on the determined pixel luminances, in particular in order to access the percentiles of luminance values. For example, the $70^{th}$ percentile of luminance values corresponds to a critical luminance value below which 70% of pixels have a luminance lower than the critical luminance value and 30% of pixels have a luminance value above the critical luminance value. The critical luminance value can then be set as the threshold luminance value.

Figure 5B:
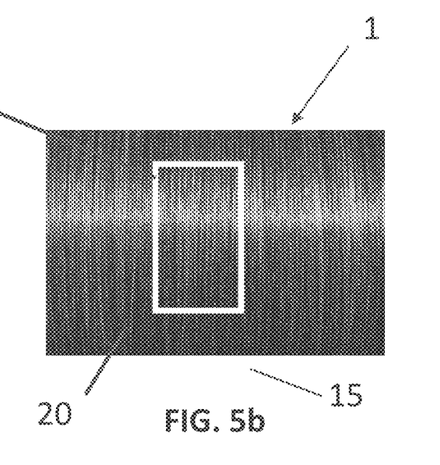

FIG. 5b shows strand of hair 1 known to have a greyness level of 50%. Image 15 is a greyscale image of image 11.

Figures 5C, 5D:
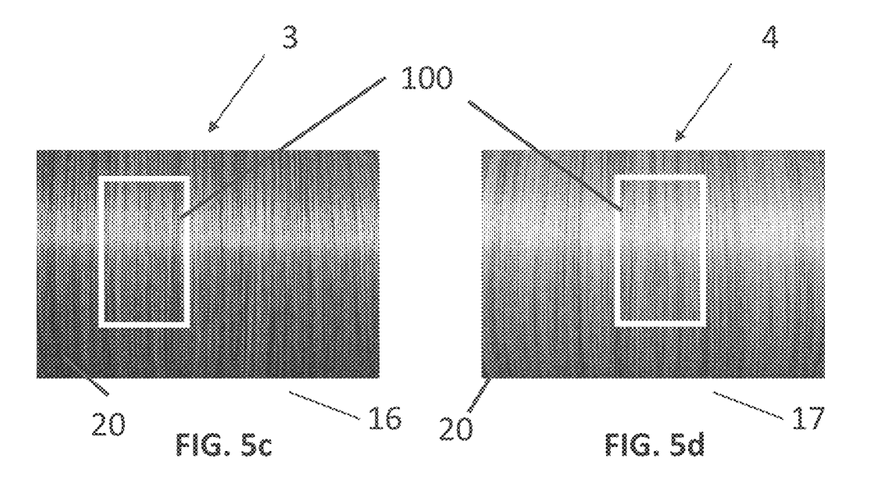

FIG. 5c shows a reference strand of hair 3 known to have a greyness level of 70%. In other words, 30% of the hair fibers are pigmented and 70% of the hair fibers in this reference strand of hair 3 are white hair fibers. The steps described in connection with FIG. 5a are here repeated by setting the critical luminance value at the luminance value observed for the $30^{th}$ percentile of luminance values.

FIG. 5d shows a reference strand of hair 4 known to have a greyness level of 90%. In other words, 10% of the hair fibers are pigmented and 90% of the hair fibers in this reference strand of hair 4 are white hair fibers. The steps described in connection with FIG. 5a are here repeated by setting the critical luminance value at the luminance value observed for the $10^{th}$ percentile of luminance values.

The critical threshold values obtained from images 14-17, without restricting the images to a preferred portion, leads to some differences in the critical luminance value. For image 14 the critical luminance value is identified as being equal to 72, for image 15, the critical luminance value is identified as being equal to 65, for image 16 the critical luminance value is identified as being equal to 76 and for image 17 the critical luminance value is identified as being equal to 85. A better choice for the threshold luminance value can be set at the average of these four values, all close to 75.

Differences between critical threshold values can be reduced by a careful selection of a smaller portion 100, such as the one represented with a white square on FIGS. 2a-2d.

The threshold luminance value can then be used to identify and count the number of pixels corresponding to white hair fibers on any other image of a strand of hair of unknown greyness.

The method of the present disclosure outputs a greyness level of the strand of hair. This information can be used in order to make customized hair treatment product recommendations for example. Typically, once the greyness level of a user is known, it can trigger a selection of hair coloration treatments or shampoos that are compatible with the determined greyness level. The output of the product recommendation, or the output of the determined greyness level can be done via a man machine interface, in visual form or in audible form. Additionally, such a man-machine interface may receive inputs from a user, in written form, via selection from menus displayed to the user or orally by dictating selections or by orally communicating with a software assisted interface.

The steps of the examples and embodiments described above can be implemented by a processor such as a computer. A computer program product comprising steps of the above-described method can be used to implement the method on a computer.

Different types of non-transitory computer readable storage mediums on which a computer program comprising instructions to implement the method of the present disclosure can be used. These could for example comprise a processor or chip, an electronic circuit comprising several processors or chips, a hard drive, a flash or SD card, a USB stick, a CD-ROM or DVD-ROM or Blue-Ray disc, or a diskette or floppy disk.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for determining a greyness level of a strand of hair, the method comprising:
    obtaining an image of the strand of hair, the image representing the strand of hair according to a predefined representation standard, the image comprising a portion representing the strand of hair with pixels;
    determining, for each pixel of the portion, a luminance value;
    obtaining an image of a reference strand of hair of known greyness level, the image of the reference strand of hair representing the reference strand of hair according to the predefined representation standard, the image of the reference strand of hair comprising a reference portion representing the reference strand of hair with pixels;
    determining, for each pixel of the reference portion, a luminance value;
    arranging the determined luminance values of the reference portion according to percentiles;
    setting a threshold luminance value as being a luminance value observed for a percentile of luminance values equal to a total percentage of pigmented hair fibers in the reference strand of hair;
    determining an amount of pixels in the portion for which the determined luminance value is above the threshold luminance value; and
    determining the greyness level of the strand of hair by estimating a ratio of the determined amount of pixels having the luminance value above the threshold luminance value over a total amount of pixels in the portion.

2. The method of claim 1, wherein the threshold luminance value is set as a median luminance value measured on the image of the reference strand of hair, the reference strand of hair having a known proportion of white hair fibers equal to about 50% of a total amount of hair fibers in the reference strand of hair.

3. The method of claim 1, further comprising:
    obtaining at least two reference strands of hair of different and known greyness;
    obtaining, for each reference strand of hair of the at least two reference strands of hair, an image representing the reference strand of hair according to the predefined representation standard, the images of the at least two reference strands of hair comprising reference portions representing the at least two reference strands of hair with pixels;
    determining, for each pixel of the reference portion of each image of the images of the at least two references strands of hair, a luminance value;
    arranging, for the reference portion of each image of the images of the at least two reference strands of hair, the determined luminance values according to percentiles;
    determining, for the reference portion of each image of the images of the at least two reference strands of hair, a critical luminance value as being a luminance value observed for a percentile of luminance values equal to a total percentage of pigmented hair fibers in the reference strand of hair; and
    setting the threshold luminance value as being an average value of the critical luminance values.

4. The method of claim 3, wherein the threshold luminance value is set using at least five reference strands of different and known greyness levels.

5. The method according to claim 3, further comprising:
    setting the threshold luminance value using each reference strand of hair of a set of reference strands of hair of known greyness value, wherein the set of reference strands of hair comprise different hair colors.

6. The method according to claim 1, further comprising:
    converting a color of each pixel inside the portion of the image into a greyscale.

7. The method according to claim 1, further comprising:
    obtaining a raw image of the strand of hair, the raw image representing the strand of hair and a calibration bar of known dimensions and color; and
    converting the raw image to the image of the strand of hair by adjusting representation parameters of the raw image using image processing capable of modifying at least one among angle of view, magnification and luminosity of the raw image in order to represent the strand of hair according to the predefined representation standard, wherein the representation parameters comprise angle of view, magnification and luminosity.

8. The method according to claim 1, wherein the predefined representation standard comprises at least one of the following, or a combination thereof: angle of view, magnification, illumination conditions, spatial arrangement of fibers of the strand of hair, relative position of the strand of hair, and a spectrum and intensity of a light source illuminating the strand of hair.

9. The method according to claim 1, further comprising:
selecting the portion of the image representing the strand of hair with pixels, so that the portion comprises substantially parallel hair fibers.

10. The method of claim 1, further comprising:
obtaining a set of reference strands of hair comprising at least two reference strands of hair of different and known greyness;
obtaining, for each reference strand of hair of the at least two reference strands of hair, an image representing the reference strand of hair according to the predefined representation standard, the images of the at least two reference strands of hair comprising reference portions representing the at least two reference strands of hair with pixels;
determining, for each pixel of the reference portion of each image of the images of the at least two references strands of hair, a luminance value;
arranging, for the reference portion of each image of the images of the at least two reference strands of hair, the determined luminance values according to percentiles;
determining, for the reference portion of each image of the images of the at least two reference strands of hair, a critical luminance value as being a luminance value observed for a percentile of luminance values equal to a total percentage of pigmented hair fibers in the reference strand of hair; and
setting the threshold luminance value as being an average value of the critical luminance values, wherein the threshold luminance value is set using at least five reference strands of hair of different and known greyness levels, wherein the set of reference strands of hair comprise different hair colors.

11. The method of claim 10, further comprising:
obtaining a raw image of the strand of hair, the raw image representing the strand of hair and a calibration bar of known dimensions and color; and
selecting the portion of the image representing the strand of hair with pixels, so that the portion comprises substantially parallel hair fibers.

12. The method of claim 11, further comprising:
converting the raw image to the image of the strand of hair by adjusting representation parameters of the raw image using image processing capable of modifying at least one among angle of view, magnification, and luminosity of the raw image in order to represent the strand of hair according to the predefined representation standard, wherein the representation parameters comprise angle of view, magnification, and luminosity.

13. A non-transitory computer readable storage medium having stored thereon a computer program comprising instructions for execution of a method for determining a greyness level of a strand of hair according to claim 1, wherein a non-transitory data processing device, upon accessing and executing the computer program, performs the method of claim 1.

14. A system for determining a greyness level of a strand of hair, the system comprising:
an image acquisition device, configured to receive an image of the strand of hair, the image representing the strand of hair according to a predefined representation standard;
at least one non-transitory data processing device capable of receiving data from the image acquisition device and configured to:
select a portion within the image, the portion representing the strand of hair with pixels;
determine, for each pixel of the portion, a luminance value;
obtain an image of a reference strand of hair of known greyness level, the image of the reference strand of hair representing the reference strand of hair according to the predefined representation standard, the image of the reference strand of hair comprising a reference portion representing the reference strand of hair with pixels;
determining, determine, for each pixel of the reference portion, a luminance value;
arrange the determined luminance values of the reference portion according to percentiles;
set a threshold luminance value as being a luminance value observed for a percentile of luminance values equal to a total percentage of pigmented hair fibers in the reference strand of hair;
estimate an amount of pixels in the portion for which the determined luminance value is above the threshold luminance value; and
determine the greyness level of the strand of hair by calculating a ratio of the estimated amount of pixels in the portion for which the determined luminance value is above the threshold luminance value over a total amount of pixels in the portion.

15. The system according to claim 14 further comprising:
a position selection mechanism, adapted to receive the image acquisition device and set it at a predefined distance, predefined position and predefined angle with respect to the strand of hair.

16. The system of claim 15, further comprising:
a light source, the light source being arranged at a predefined distance, predefined position and predefined angle with respect to the strand of hair and configured to emit light having predefined properties, selected from at least one of the following: spectrum of emitted light and intensity of emitted light.

17. The system of claim 16, further comprising:
a substrate comprising a curved surface, the curved surface being configured to receive the strand of hair.

18. The system according to claim 14 further comprising:
a light source, the light source being arranged at a predefined distance, predefined position and predefined angle with respect to the strand of hair and configured to emit light having predefined properties, selected from at least one of the following: spectrum of emitted light and intensity of emitted light.

19. The system according to claim 14 further comprising:
a substrate comprising a curved surface, the curved surface being configured to receive the strand of hair.

* * * * *